United States Patent
Powers et al.

(10) Patent No.: US 6,888,038 B2
(45) Date of Patent: May 3, 2005

(54) ENHANCED PRODUCTION OF LIGHT OLEFINS

(75) Inventors: Donald H. Powers, Pearland, TX (US); Kenneth M. Webber, Friendswood, TX (US)

(73) Assignee: Equistar Chemicals, LP, Houston, TX (US)

( * ) Notice: Subject to any disclaimer, the term of this patent is extended or adjusted under 35 U.S.C. 154(b) by 99 days.

(21) Appl. No.: 10/100,522

(22) Filed: Mar. 18, 2002

(65) Prior Publication Data

US 2003/0181777 A1 Sep. 25, 2003

(51) Int. Cl.$^7$ .................................................. C07C 4/06
(52) U.S. Cl. ........................ 585/648; 585/649; 585/650; 585/651
(58) Field of Search ................................ 585/648, 649, 585/650, 651

(56) References Cited

U.S. PATENT DOCUMENTS

| | | | |
|---|---|---|---|
| 4,016,275 A | | 4/1977 | Moore ........................ 424/251 |
| 4,044,065 A | * | 8/1977 | Butter et al. ................ 585/509 |
| 4,076,842 A | | 2/1978 | Plank et al. ................ 423/328 |
| 4,556,477 A | | 12/1985 | Dwyer ........................ 208/111 |
| 4,590,320 A | | 5/1986 | Sapre ........................ 585/324 |
| 5,026,936 A | | 6/1991 | Leyshon et al. ............ 585/315 |
| 5,043,522 A | | 8/1991 | Leyshon et al. ............ 585/651 |
| 5,177,281 A | | 1/1993 | Haag et al. ................ 585/324 |
| 5,191,142 A | | 3/1993 | Marshall et al. ............ 585/640 |
| 6,069,287 A | * | 5/2000 | Ladwig et al. .............. 585/648 |

* cited by examiner

*Primary Examiner*—Thuan D Dang
(74) *Attorney, Agent, or Firm*—Roderick W. MacDonald

(57) ABSTRACT

A method for reducing the formation of undesired heavy hydrocarbons when catalytically cracking a heavy olefin containing feed stock to a light olefin product by employing an oxygen containing hydrocarbon as a co-feed stock.

18 Claims, No Drawings

ENHANCED PRODUCTION OF LIGHT OLEFINS

BACKGROUND OF THE INVENTION

1. Field of the Invention

This invention relates to the conversion of a hydrocarbon feed stream containing heavy olefins (4 carbon atoms per molecule, viz. C4, and heavier) to a product that is enhanced with an increased content of light olefins (ethylene and propylene, C2 and C3). In particular, this invention employs an oxygen containing co-feed material along with said feed stream to reduce the formation of aromatic compounds (C6 to C8) and heavier compounds (C8 and heavier) in the light olefin rich product of this invention. Hereinafter, all specified molecular carbon atom ranges, e.g., (C6 to C8), are inclusive.

2. Description of the Prior Art

The petrochemical industry has undergone sustained growth due, in part, to the demand for many, varied polymeric products. This has led to an ever increasing demand for petrochemical raw materials such as light olefins from which to make polymeric materials such as polyethylene and polypropylene.

Heretofore light olefins have been formed by the steam cracking of ethane, propane, or heavy hydrocarbons (C5 and heavier). Also, catalytic cracking of heavy hydrocarbons has been employed, for example, fluid catalytic cracking units. There is current interest in producing higher yields of light olefins from catalytic processes. See U.S. Pat. Nos. 5,043,522 and 5,026,936, both to Leyshon et al. In some of these processes the desired predominately light olefin product of the process contains undesirable quantities of aromatics (C6 to C8) and heavier hydrocarbons (C8 and heavier).

Also heretofore methanol has been catalytically converted to light olefins and butenes. See U.S. Pat. No. 4,590,320 to Sapre. Sapre teaches the use of a very minor amount, less than 3 weight percent, of a light olefin co-feed. This co-feed is expressly taught by Sapre to be used to avoid complications in tubular reactor stability due to autocatalysis. Thus, Sapre's minor amount of light olefin co-feed is taught not to take part in the chemical reaction that produces the light olefin product, but merely to serve as a mechanical, as opposed to chemical, means to thermally stabilize the reaction system.

It has also been taught heretofore to form olefins heavier than light olefins (C3 to C12) and/or paraffinic gasoline components (C4 and heavier) from methanol. See U.S. Pat. No. 5,191,142 to Marshall et al. Marshall et al. expressly teach that their invention is operable with a feed composed 100% of methanol, because Marshall et al. believe the mechanism of their invention to be methanol alkylation. Even though the presence of olefins is not required for the operability of the Marshall et al. invention, Marshall et al. teach that if some olefins do get into the feed due to the feed being the product of another process, e.g., a Fischer-Tropsch synthesis gas conversion process, then it is necessary for the operability of their invention that the methanol concentration "throughout the reaction zone" always be 50 to 100%, with a molar ratio of methanol to olefin of 2 to 1 being preferred. Thus, Marshall et al. teach the use of a substantial excess of methanol when an olefin is present.

SUMMARY OF THE INVENTION

In accordance with this invention it has been found that, when catalytically cracking heavy olefins (C4 and heavier) in a conventional manner to form light olefins, the use of a minor amount of an oxygenated hydrocarbon co-feed along with the heavy olefins feed results in a surprising reduction in the amount of aromatics (C6 to C8) and heavier hydrocarbons (C8 and heavier) in the desired light olefin product.

Applicants have found that in the catalytic cracking of a feed containing heavy olefins to light olefins a minor amount of an oxygenated compound co-feed yields surprising results by unexpectedly decreasing the amount of certain undesirable compounds normally formed in the cracking process and found in the cracking process product, thereby producing a final product that has more light olefins and less undesired hydrocarbons than normally obtained by a conventional cracking process.

DETAILED DESCRIPTION OF THE INVENTION

In this invention a hydrocarbon feed material or stream containing at least some heavy olefins (C3 and heavier) is thermally cracked catalytically to form a product rich in light olefins but containing some undesirable hydrocarbons. By this invention the amount of undesirable hydrocarbon in said product is substantially reduced by deliberately employing along with said feed stream (feed) to said catalytic cracker, a co-feed stream (co-feed) which contains at least one oxygen containing hydrocarbon. The co-feed is employed with a minor molar amount of oxygen containing hydrocarbon with respect to the moles of olefinic feed, such minor molar amount being effective to reduce the amount of said undesirable hydrocarbons in the light olefin product below the amount of undesirable hydrocarbons that would normally have been found in such final product had no oxygen containing hydrocarbon been employed in the process.

The feed used as a starting material in this invention is primarily a hydrocarbon mixture that contains at least in part heavy olefins (C4 and heavier), linear and/or branched, and having no effective amount of oxygen containing hydrocarbon. The heavy olefins preferably have 4 or 5 carbon atoms per molecule (C4 and C5 olefins), and a single carbon-carbon double bond. Representative specific heavy olefins include 1-butene, cis-2-butene, trans-2-butene, isobutene, 1-pentene, cis-2-pentene, trans-2-pentene, 3-methyl-1-butene, 2-methyl-2-butene, 2-methyl-1-butene, and mixtures of two or more thereof. The feed can contain other hydrocarbons, but it is preferably at least about 40% by weight, more preferably at least about 60% by weight, of heavy olefins. Such feeds can come from fluid catalytic crackers, hydrocarbon pyrolysis units, or the like. A preferred feed consists essentially of C4 and/or C5 olefins.

The feed is conventionally converted to ethylene and/or propylene (C2 and/or C3 light olefins) by contacting it with a catalyst under reaction conditions effective for the formation of light olefins, and preferably favoring the formation of light olefins. Such catalysts and reaction conditions are well known in the art. See the Leyshon et al. patents cited hereinabove.

The goal for the catalytic cracking process is to obtain a product having as high a light olefin content as possible. However, the product often contains other hydrocarbons that are undesired in a light olefin product, namely aromatic compounds (C6 to C8) and/or heavier hydrocarbons (C8 and heavier).

This invention substantially decreases the amount of said undesired compounds in a light olefin product of a hydrocarbon catalytic cracking process.

The catalysts used in this invention can vary widely and will be obvious to those skilled in the art since they need only be effective for the formation of light olefins. Preferred catalysts are the zeolites, natural or synthetic. Useful zeolites are numerous and well known in the cracking art. See U.S.

Pat. No. 5,026,936. Suitable zeolites have pores (channels) large enough both to admit heavy hydrocarbons, particularly heavy olefins, more particularly C4 and C5 olefins; and to allow light olefins to diffuse out. Preferably, the pores are small enough both to retard dimerized products from diffusing out and to minimize the formation of hydrocarbon coke precursors within the catalyst. The zeolites are often used in powder, pellet or other known physical form. Optionally they are combined with one or more binders such as natural clays, silicas, aluminas, and the like as is well known in the art. Useful zeolite catalysts have a pore size index range of from about 22.6 to about 29, "pore size index" meaning the mathematical product of the dimensions in Angstroms of the two major axes of the pores. This index is well known, see U.S. Pat. No. 5,177,281. Useful catalysts can also have silica/alumina ratios of from about 15/1 to about 200/1. Suitable specific catalysts include MTT, MFI, and FER. Preparation of these catalysts is well known, see U.S. Pat. Nos. 4,076,842; 4,556,477; and 4,016,275 for representative preparation processes.

The cracking process can be carried out in a batch, continuous, semi-batch or semi-continuous manner using conventional reactor systems such as fixed bed, moving bed, fluidized bed and the like; fixed bed being presently preferred. Conventional catalyst regeneration techniques can also be employed.

The feed and co-feed are contacted with the catalyst under reaction conditions effective to form light olefins, and preferably favoring light olefins. Contacting is preferably done in the vapor phase by bringing vaporous feed and co-feed into contact with the solid catalyst. The feed, co-feed, and/or catalyst can be preheated as desired. The reaction is performed at a temperature of from about 400° F. to about 1200° F., preferably from about 800° F. to about 1100° F., at pressures from about zero to about 150 psig, preferably from about zero to about 50 psig, and weight hourly space velocity feed rates from about 1 to about 100 $h^{-1}$, preferably from about 3 to about 15 $h^{-1}$, with or without a conventional diluent. The co-feed flow rate can be from about 1 to about 57% of the feed rate, preferably from about 25% to about 50% of the feed rate.

The co-feed can be one or more oxygen containing compounds from the group comprising alcohols, preferably C1 to C5, ketones, preferably C3 to C5, ethers, preferably C2 to C6, carboxylic acids, preferably C2 to C4, polyols, preferably C1 to C5, aldehydes, preferably C1 to C5, cyclic ethers, preferably C4 to C6, epoxides, preferably C2 to C4, and mixtures of two or more thereof. A preferred group consists essentially of alcohols, ketones, ethers, and carboxylic acids, with alcohols the most preferred. Representative specific compounds include methanol, ethanol, isopropanol, ethylene glycol, propyleneglycol, acetaldehyde, propionaldehyde, acetone, methylethylketone, dimethylether, diethylether, methyltertiarybutylether, tertamylmethylether, tetrahydrofuran, dioxane, ethylene oxide, propylene oxide, acetic acid, propionic acid, formic acid, and butyric acid.

The amount of oxygen containing hydrocarbon used in this invention can vary widely, but is a minor amount on a weight or molar basis compared with the olefinic feed. Generally, the molar ratio of oxygen containing hydrocarbon in the co-feed to the olefins in the feed is, at a minimum, a ratio effective to reduce the amount of aromatics and/or heavier hydrocarbons aforesaid below that which would normally be found in a light olefin product derived from the same feed material under the same reaction conditions and in the absence of an effective amount of oxygen containing hydrocarbon. The molar ratio of oxygen containing hydrocarbon to olefinic feed aforesaid is preferably less than about 1/1, still more preferably from about 4/5 to about 1/4.

The co-feed can, if desired, carry other materials that do not materially interfere with the desired reaction such as diluents and the like.

Generally the feed streams useful in this invention contain no oxygen containing hydrocarbons. In the unlikely event that a feed should contain trace or ineffective amounts of oxygen containing hydrocarbon, these amounts can be taken into account when designing the co-feed to be used with that particular feed.

By following the teachings of this invention the amount of undesired aromatics and/or heavier hydrocarbons in a light olefin cracking product can be substantially reduced as shown in the following examples.

EXAMPLE 1

A sample of MTT zeolite powder was pressed into pellets. The pellets were broken into pieces and sieved. The zeolite pieces that were retained between 12 and 20 mesh screens were used as the catalyst. A fixed bed reactor was loaded with 3.05 grams of this catalyst. The catalyst was dried prior to contacting it with hydrocarbon. The drying procedure consisted of purging the reactor with nitrogen while holding the bed for one hour at 180° F., one hour at 195° F., one hour at 220° F., and three hours at 482° F. At that time, nitrogen flow was stopped and the reactor heated to 1160° F. When the reactor temperature reached 1022° F., hydrocarbon flow was started to the reactor at approximately 9.2 g/hr. The hydrocarbon used for this first experiment was a conventional steam cracker $C_4$ Raffinate-2, whose major components are listed in the following table:

| Component | Concentration, Wt % |
| --- | --- |
| Isobutane | 3.65 |
| 1-Butene | 38.19 |
| n-Butane | 24.6 |
| Trans 2-Butene | 19.58 |
| Cis 2-Butene | 13.47 |

Periodically, the effluent from the reactor was analyzed by gas chromatography (GC) to determine the composition of the product. The variables followed for this study are the ratio of less desirable by-products (such as $C_6$–$C_8$ aromatics or material heavier than $C_8$) to the production of targeted products, namely ethylene and propylene. The following table lists some of the essential reaction parameters at the time of the analysis along with compositional data, as determined by GC:

| | | | |
| --- | --- | --- | --- |
| Time on Stream, Hrs. | 4.2 | 6.1 | 8.0 |
| Reactor Temperature, ° F. | 1168 | 1168 | 1168 |
| Weight Hourly Space Velocity (WHSV) | 3.0 | 3.0 | 2.9 |
| ($C_6$–$C_8$ Aromatics)/($C_2$ + $C_3$ Olefins) | 0.314 | 0.243 | .177 |
| ($C_8$+ Material)/($C_2$ + $C_3$ Olefins) | 0.147 | 0.069 | .040 |

EXAMPLE 2

The run of Example 1 was continued. At 8.1 hours, flow of methanol was started to the reactor. Product effluent samples were analyzed by gas chromatography, as in the first example. The methanol had a surprising and dramatic impact on the product distribution. The results are shown in the following table:

| Time on Stream, Hrs. | 12.0 | 18.8 | 24.8 |
|---|---|---|---|
| Reactor Temperature, ° F. | 1168 | 1167 | 1168 |
| Olefinic Stream WHSV | 3.0 | 3.0 | 2.9 |
| Methanol WHSV | 1.3 | 1.3 | 1.3 |
| ($C_6$–$C_8$ Aromatics)/($C_2$ + $C_3$ Olefins) | 0.081 | 0.036 | 0.093 |
| ($C_8$+ Material)/($C_2$ + $C_3$ Olefins) | 0.001 | 0.0003 | 0.006 |
| Methanol/Olefinic Stream Mole Ratio | 0.762 | 0.762 | 0.788 |

EXAMPLE 3

The run of Examples 1 and 2 was continued. At 25.4 hours into the run, the olefinic hydrocarbon flow was stopped and the methanol flow was increased.

| Time on Stream, Hrs. | 30.8 |
|---|---|
| Reactor Temperature, ° F. | 1172 |
| Olefinic Stream WHSV | 0 |
| Methanol WHSV | 2.6 |
| ($C_6$–$C_8$ Aromatics)/($C_2$ + $C_3$ Olefins) | 0.984 |
| ($C_8$+ Material)/($C_2$ + $C_3$ Olefins) | 0.188 |

This example demonstrates that the effect of the methanol is synergistic with the olefinic hydrocarbon. Neither methanol, nor olefinic hydrocarbon by themselves can produce as low a ratio of undesirable products to desirable products as can the combination of methanol and olefinic hydrocarbon.

EXAMPLE 4

The run of Examples 1, 2, and 3 was continued. At 33.9 hours into the run, the flow of methanol was stopped and a second olefinic stream was started to the reactor. The composition of this second olefinic hydrocarbon stream is given below:

| Component | Concentration, Wt % |
|---|---|
| 1-Octene | 73.6 |
| 1-Decene | 19.1 |
| 2,4,4 Trimethyl 1-Pentene | 7.3 |

Product effluent analyses were conducted by GC and the results are presented in the following table:

| Time on Stream, Hrs. | 48.5 | 50.5 | 52.4 |
|---|---|---|---|
| Reactor Temperature, ° F. | 1168 | 1168 | 1167 |
| Weight Hourly Space Velocity (WHSV) | 2.0 | 2.6 | 4.3 |
| ($C_6$–$C_8$ Aromatics)/($C_2$ + $C_3$ Olefins) | 0.186 | 0.215 | 0.168 |
| ($C_8$+ Material)/($C_2$ + $C_3$ Olefins) | 0.031 | 0.054 | 0.087 |

These results show that the methanol must be present to gain the synergistic effect. If the methanol flow is stopped, the catalyst soon reverts to its earlier selectivity by producing larger quantities of aromatics and higher molecular weight species per unit production of light olefins.

What is claimed is:

1. In a method for forming a light olefin product by the catalytic cracking of a hydrocarbon feed that contains at least in part a mixture of heavy olefins using both a catalyst system and reaction conditions effective for the formation of light olefins, the improvement comprising, co-feeding along with said hydrocarbon feed to said catalytic cracking a minor effective amount of at least one oxygen containing hydrocarbon selected from the group consisting of alcohols, ketones, ethers, carboxylic acids, polyols, aldehydes, cyclic ethers, epoxides, and mixtures of two or more thereof, whereby aromatics and/or C8 and heavier hydrocarbons in said light olefin product are reduced in amount below what they would have been had the oxygen containing compound not been employed.

2. The method of claim 1 wherein said hydrocarbon feed is composed in substantial amount of C4 and C5 hydrocarbons.

3. The method of claim 1 wherein said hydrocarbon feed consists essentially of C4 and C5 paraffins and C4 and C5 olefins.

4. The method of claim 1 wherein said catalyst system that favors the formation of light olefins and consists essentially of zeolite having a pore size index range from about 14 to about 29.

5. The method of claim 1 wherein said catalyst system is essentially MTT.

6. The method of claim 1 wherein said catalytic cracking reaction conditions are a temperature in the range from about 400° F. to about 1200° F., a pressure in the range from about zero psig to about 150 psig, and the weight hourly space velocity of both the feed and co-feed are from about 1 to about 100 $h^1$ with the co-feed rate being from about 1 to about 57% of the feed.

7. The method of claim 1 wherein said oxygenated hydrocarbon is selected from the group consisting of alcohols (C1 to C5), ketones (C3 to C5), ethers (C2 to C6), carboxylic acids (C2 to C4), polyols (C1 to C5), aldehydes (C1 to C5), cyclic ethers (C4 to C6), epoxides (C2 to C4), and mixtures of two or more thereof.

8. The method of claim 1 wherein said oxygenated hydrocarbon is selected from the group consisting of alcohols (C1 to C5), ketones (C3 to C5), ethers (C2 to C6), carboxylic acids (C2 to C4), and mixtures of two or more thereof.

9. The method of claim 1 wherein said co-feed comprises at least one alcohol (C2 to C5).

10. The method of claim 1 wherein said oxygen containing hydrocarbon in said co-feed is present in the total combination of feed and co-feed in a minor molar amount that is substantially less than an equimolar ratio of oxygen containing hydrocarbon to olefins in said feed.

11. The method of claim 1 wherein said oxygen containing hydrocarbon is present in the total combination of feed and co-feed in a molar ratio of oxygen containing hydrocarbon to olefinic feed of less than about 1/1.

12. The method of claim 1 wherein said oxygen containing hydrocarbon is present in a molar ratio of oxygen containing hydrocarbon to olefinic feed of from about 4/5 to about 1/4.

13. The method of claim 1 wherein said feed contains at least 40% by weight of C4 and C5 hydrocarbons, said catalyst system consists essentially of zeolite, said co-feed is selected from the group consisting of alcohols (C1 to C5), ketones (C3 to C5), ethers (C2 to C6), carboxylic acids (C2 to C4), and mixtures of two or more thereof, and said co-feed is employed in a molar ratio of oxygen containing hydrocarbon to olefinic feed of less than about 1/1.

14. The method of claim 1 wherein said feed consists essentially of olefins (C4 and C5), said catalyst system is at least one zeolite that favors the formation of light olefins and has a pore size index of from about 14 to about 29, said co-feed is selected from the group consisting of alcohols having from 1 to 5 carbon atoms per molecule, and said oxygen containing hydrocarbon is present in the total combination of co-feed and feed in a molar ratio of oxygen containing hydrocarbon to olefinic feed of from about 4/5 to about 1/4.

15. The method of claim 14 wherein said feed consists essentially of isobutane, 1-butene, n-butane, trans 2-butene, cis 2-butene, and mixtures of two or more thereof.

16. The method of claim 15 wherein said catalyst is MTT.

17. The method of claim 16 wherein said co-feed consists essentially of methanol.

18. The method of claim 14 wherein the catalytic cracking is carried out in a fixed bed reactor.

* * * * *